United States Patent [19]

Jungmann

[11] Patent Number: 4,637,381

[45] Date of Patent: Jan. 20, 1987

[54] FOOT SUPPORTING DEVICE

[75] Inventor: Gertrude Jungmann, Rangeley, Me.

[73] Assignee: Institute for Gravitational Strain Pathology, Inc., Rangeley, Me.

[21] Appl. No.: 740,746

[22] Filed: Jun. 3, 1985

[51] Int. Cl.⁴ .............................................. A61F 5/00
[52] U.S. Cl. .................................... 128/80 G; 36/91; 128/81 R
[58] Field of Search .............. 128/80 R, 81 R, 80 D, 128/80 G; 36/91

[56] References Cited

U.S. PATENT DOCUMENTS

| | | | |
|---|---|---|---|
| 1,245,468 | 11/1917 | Koppe | 128/81 R |
| 1,373,211 | 3/1921 | Tanner | 128/81 R |
| 1,566,063 | 12/1925 | Barry | 128/80 D |
| 2,596,038 | 5/1952 | Mayer | 128/81 R |
| 2,708,930 | 5/1955 | Lowman | 128/80 D |
| 3,556,091 | 1/1971 | Haig | 128/80 G X |

FOREIGN PATENT DOCUMENTS

| | | | |
|---|---|---|---|
| 533712 | 9/1931 | Fed. Rep. of Germany | 128/81 R |
| 838481 | 5/1952 | Fed. Rep. of Germany | 128/81 R |
| 95298 | 7/1922 | Switzerland | 128/81 R |
| 241733 | 10/1925 | United Kingdom | 128/81 R |

*Primary Examiner*—Edgar S. Burr
*Assistant Examiner*—Moshe I. Cohen
*Attorney, Agent, or Firm*—Goodman & Teitelbaum

[57] ABSTRACT

A foot supporting device for pulling the foot muscles back to a relaxation phase intermediate stress phases placed on the foot. The device includes a heel strap which is placed over the heel portion of the foot. An instep strap is placed around the lower instep portion of the foot. Elastic bands extend between the heel strap and the instep strap. The elastic bands pass through a connecting member and are received in an adjusting member whereby adjustment can be made to the tension in the bands, so as to control the pull between the instep strap and the heel strap. A toe strap is elastically coupled to the connecting member for placement around the big toe of the foot. A wire member is connected between the instep strap and the toe strap and placed between the big toe and the second toe of the foot.

9 Claims, 7 Drawing Figures

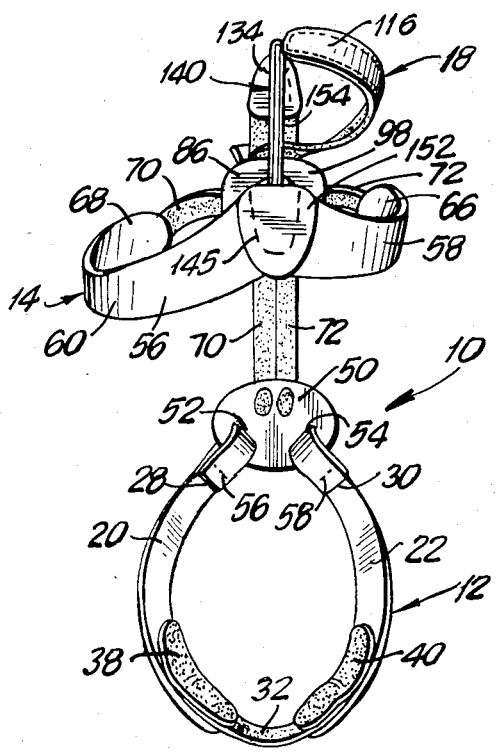
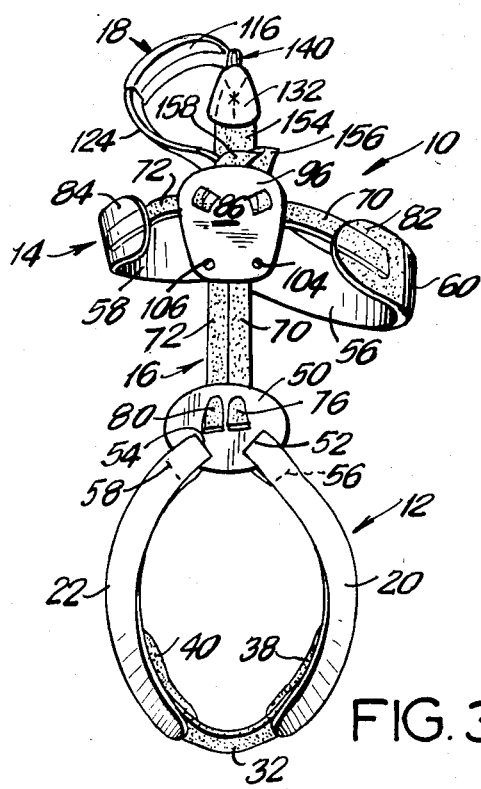
FIG. 2    FIG. 3
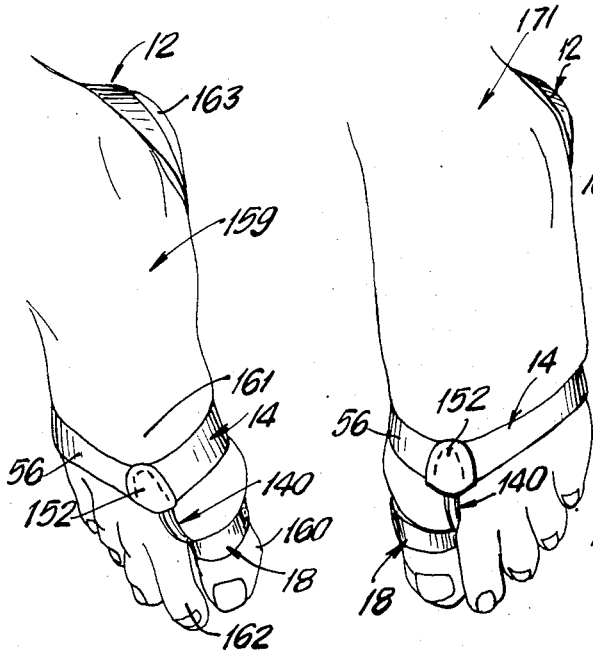
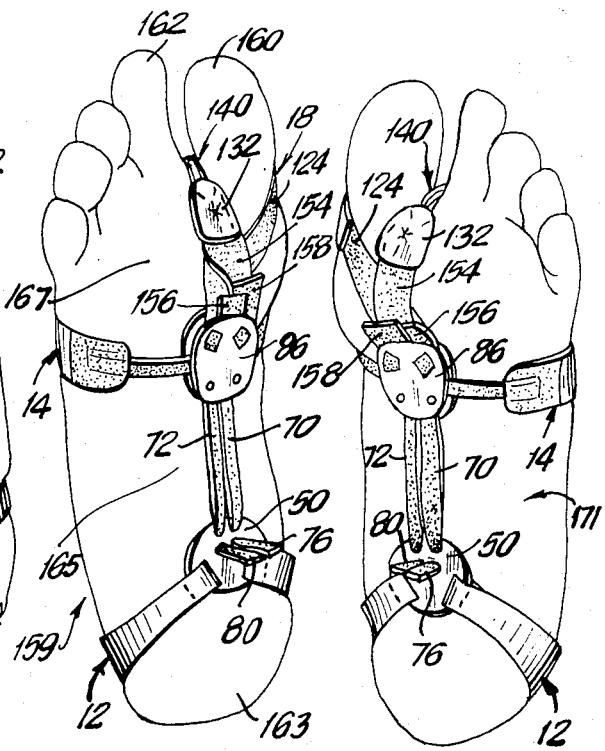
FIG. 4    FIG. 5    FIG. 6    FIG. 7

FOOT SUPPORTING DEVICE

BACKGROUND OF THE INVENTION

This invention relates to foot supporting devices and, more particularly, to a device for pulling the foot muscles back to a relaxation phase in between times that the foot is stressed.

For continuous efficiency of the foot muscles, it is important to maintain a smooth alternating action between tension and relaxation of the muscles. During tension, the foot is under stress. Such tension occurs when the foot is in a weight-bearing condition. Relaxation of the foot muscles should take place when lifting the foot in between steps. If the foot remains stiff during such relaxation phase, the muscles tire and become stiff and painful. The important factor is to assure that an interchange of phases of stress and relaxation is automatically and mechanically regulated. It is the interaction between the relaxation and the stress phases that permits the muscles to re-energize themselves and, consequently, enables them to be ready for further demands of additional stress.

During the change between relaxation and stress, a change in the configuration of the foot occurs. However, when external conditions are present, they can restrain the foot so as to make relaxation of the foot impossible. Such external conditions include tight shoelaces, stiff or tight shoes, high heels, stiff arch supports and other similar restrictions.

As a result, even though the foot may lift off the ground during the intermediate stages between stress phases, the muscles may not have an opportunity to relax and the natural exchange between tension and relaxation is precluded.

Although exercises can be utilized to maintain the loosening and moving of the muscles, it is not always practical to prescribe loosening exercises in the majority of the cases, and, accordingly the muscles frequently remain fatigued and actually lose their ability to relax thereby staying tense and eventually cramp up.

Various foot straps have been provided in the prior art which are applied to the foot for the purpose of correcting various foot weaknesses and toe deformities. For example, U.S. Pat. No. 3,556,091 describes a toe holder having a continuous strap fitting around the heel portion and terminating in a pair of toe loops so as to grasp two toes and maintain them in appropriate configuration. While this device may be used to correct disfiguration of toes and serve as a relief for corns and calluses, it does little to provide a relaxation of the muscles and does not achieve a return of the muscles to their relaxed condition between intermediate stress phases.

SUMMARY OF THE INVENTION

Accordingly, it is an object of the present invention to provide a foot supporting device which avoids the aforementioned problems of prior art devices.

Another object of the present invention is to provide a foot supporting device for pulling of the foot muscles back into a relaxation phase intermediate various stress phases placed on to the foot muscles.

A further object of the present invention is to provide a foot supporting device which automatically brings about the recovery phase of the foot by providing the loosening movements to the foot muscles after a stress phase.

Still a further object of the present invention is to provide an automatic control of the muscle action of the foot so as to prevent overtiring of the muscles.

Yet a further object of the present invention is to provide a foot supporting device which permits foot recovery following a stresss phase.

Another object of the present invention is to provide a foot supporting device which establishes a smooth rhythm of tension and relaxation between steps so as to return the foot to a relaxation phase following its weight-bearing phase.

The present invention describes a device which operates on a system of unelastic and elastic pulls, combined in a certain way so that the elastic pulls stretch under stress and attempt to return to the starting position when the stress stops. The device provides a loosening movement of the muscles so as to lead to a relaxation phase. When the stress stops, the elastic pulls take the bony points in the foot and moves them back to their relaxed phase, thereby producing the loosening movement that leads to relaxation of the muscles.

Briefly, in accordance with the present invention, there is provided a foot supporting device for pulling the foot muscles back to a relaxation phase intermediate stress phases placed onto the foot muscles. The device includes a heel strap which is placed over the heel portion of the foot. An instep strap is provided for placement around the lower instep portion of the foot. Elastic bands are coupled between the heel strap and the instep strap and extend across the sole portion of the foot. As the elastic bands extend along the foot, they pass through a connecting member and are finally received in an adjustment member. The adjustment member provides adjustment of the tension in the bands to thereby control the pull between the instep strap and the heel strap. There is also provided a toe strap which is elastically coupled to the connecting member and is placed around the big toe of the foot. A wire member is coupled between the instep strap and the toe strap for placement between the big toe and the second toe of the foot.

The device is worn directly on the bare foot. It is fitted individually and its elastic system needs periodic adjustment according to the changes in the foot. Such fitting and adjustment is typically made by a medical doctor or anyone who been properly trained in connection with such devices.

BRIEF DESCRIPTION OF THE DRAWINGS

In the drawings:

FIG. 2 is a top view of the assembled foot supporting device;

FIG. 3 is a bottom view of the device shown in FIG. 2;

FIG. 4 shows the top view of a right foot wearing the device of the present invention;

FIG. 5 shows a top view of a left foot wearing the device of the present invention;

FIG. 6 shows the bottom view of a right foot wearing the device of the present invention; and FIG. 7 is the bottom view of a left foot wearing the device of the present invention.

In the various figures of the drawing, like reference characters designate like parts.

DESCRIPTION OF THE PREFERRED EMBODIMENT

Figure 1:
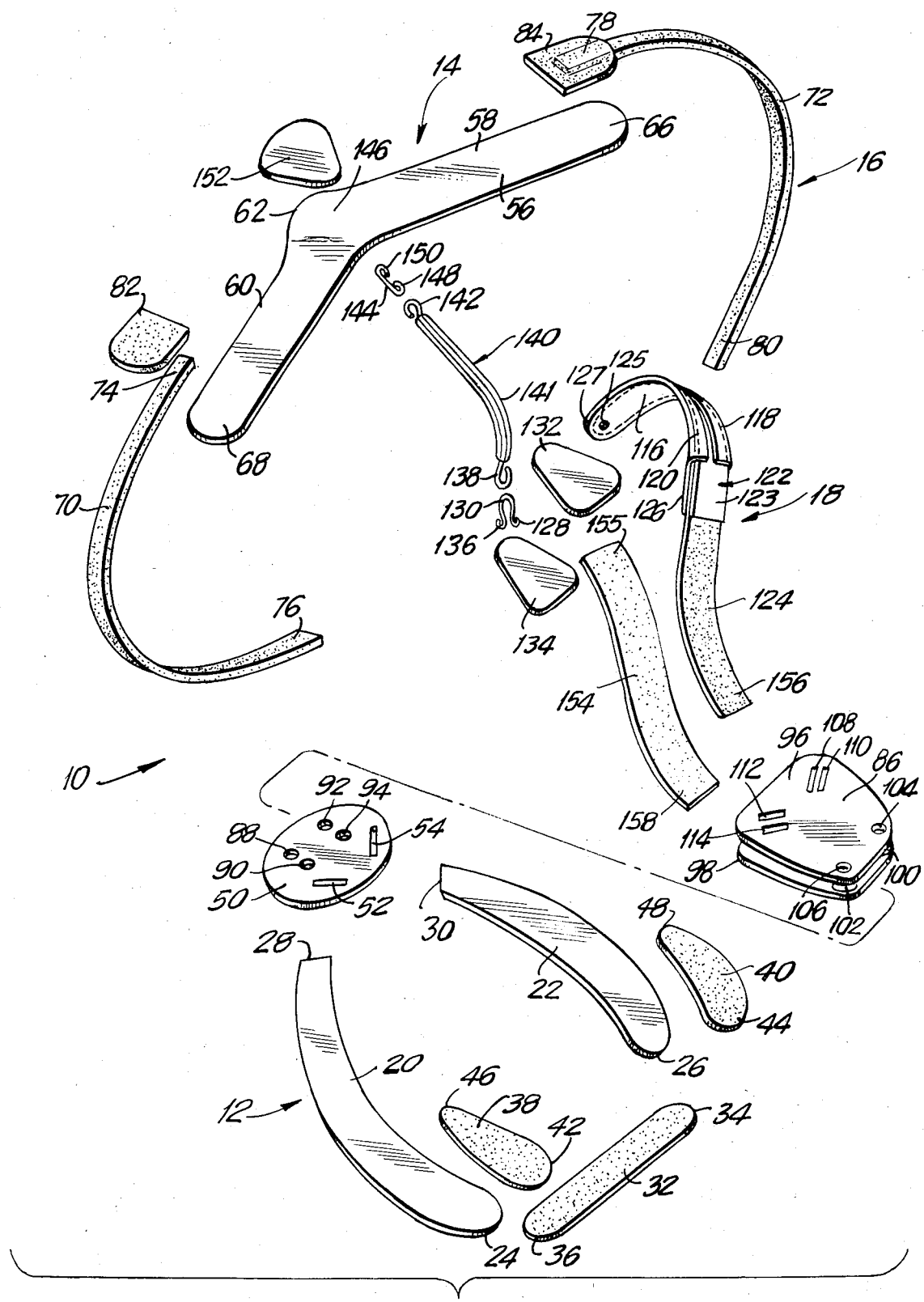
FIG. 1 is a perspective exploded view of the various parts of the foot supporting device in accordance with the present invention.

Referring now to FIGS. 1-3, the foot suppporting device of the present invention is shown generally at 10 and comprises a heel strap, shown generally at 12, an instep strap, shown generally at 14, a pair of connecting bands, shown generally at 16, and a toe strap, shown generally at 18.

More specifically, the heel strap 12 is formed as a composite of a first pair of opposing arcuate strips of material 20, 22 typically leather. The strips 20, 22 are thin and terminate at their rearward end in a rounded edge 24, 26 while their forward ends 28, 30 terminate in a flat inwardly angled cut.

The elongated leather strips 20, 22 are interconnected at the ends 24, 26 by means of an elongated band of thin elastic material 32, such as rubber, having opposing rounded lateral ends 34, 36. The elastic strip 32 is secured to the leather strips 20, 22 by means of elastic sealing tabs 38, 40 such as rubber. The sealing tabs 38, 40 have rounded rear edges 42, 44 and pointed forward edges 46, 48. These tabs can be glued or heat-sealed onto the leather sandwiching the ends 34, 36 between the tabs 38, 40 and the leather strips 20, 22.

As a result of the connection between the leather strips 20, 22 and the elastic band 32, the heel strap becomes inwardly bowed so as to have the inner surfaces thereof slightly facing each other, as shown in FIG. 2. This provides necessary curvature to facilitate placing the heel strap around the heel portion of the foot.

The heel strap 12 is secured to an adjustment member 50 formed of a thin substantially circular plate of flat stiff material, such as fiber or the like. The adjusting member 50 includes a pair of angularly directed slits 52, 54 for receiving the ends 28, 30 of the respective elongated leather strips 20, 22. The ends 28, 30 can be folded over onto itself and secured in place by means of the stitching 56, 58 so that the leather-elastic heel strap can pivot within the apertures 52, 54 and yet remain secured to provide a continuous circular configuration for fitting onto the heel of the foot.

The instep strap is formed of a substantially thin, flat leather strip 56 having a slight inverted V-shaped configuration with its two legs 58, 60 being widely angled with respect to each other. The two legs 58, 60 are joined at a central vertex portion 146 which projects forwardly into a knob 62. The entire strip 56 is of contiguous material throughout. The leather strip 56 has its lateral opposing ends 66, 68 terminating in rounded edges.

The instep strap 14 is completed by means of a pair of opposing elastic bands 70, 72, such as rubber bands. Band 70 has opposing distal ends 74, 76. Likewise elastic bands 72 has a pair of opposing distal ends 78, 80. Distal end 74 of elastic band 70 is secured to the end 68 of the leg 60 by means of a tab 82 of elastic material, such as rubber, which serves as a securing means onto the leather 56. The rubber tab 82 can be glued or heat-sealed onto the inside of the leather sandwiching the end 74 between the tab 82 and the end 68 of the leather strip 56. Similarly, a tab 84 serves to secure the distal end 78 onto the end 66 of the leather strip 56.

The elastic bands 70, 72 serve to complete the encircling of the instep portion of the foot. These bands then pass through a connecting member 86 which serves to guide the elastic bands 70, 72 into a direction-changing orientation to direct them longitudinally along the sole of the foot toward the adjusting member 50.

The adjusting member 50 includes a first pair of apertures 88, 90 and an opposing second pair of apertures 92, 94. The distal end 76 of the elastic band 70 passes into the aperture 88 and back outward through the aperture 90 so as to have the distal end 76 projecting outwardly from the adjusting member 50. Similarly, the distal end 80 passes through the aperture 92 around the underside of the adjusting member 50 and outwardly through the aperture 94 so as to have the distal end 80 projecting outwardly from the member 50.

By pulling on the ends 76, 80 through their respective apertures, the tension on the elastic bands 70, 72 can be adjusted and controlled, as desired, so as to place additional stress or tension between the instep strap 14 and the heel strap 12.

The connecting member 86 comprises a pair of opposing substantially identical thin plates 96, 98 which are spaced apart by means of opposing roller-spacers 100, 102 which are secured between the upper and lower plated 96, 98 by means of rivets 104, 106. A pair of inwardly angled slits 108, 110 are formed on one lateral side of the plate 96 and on the opposite lateral side a corresponding pair of inwardly angled slits 112, 114 are also provided.

The elastic bands 70, 72 enter between the plates 96, 98 from the lateral sides and pass around the rollers 100, 102 so as to leave from the rear end of the connecting member 86. The elastic bands 70, 72 are free to move within the connecting member 86 as they are adjusted by means of the adjustment member 50.

The toe strap 18 is formed of an elongated strip of leather material 122 covered by a cushioned material 116, such as a felt strip. The cushioning can be reinforced by making the material a double layer, by folding the cushioning material 116 over the lateral edges of the leather material 122 and securing the materials 116, 122 together by means of the stitching 118, 120. A portion 123 of the strip of leather material 122 extends from one end of the cushioned material 116. A strip of elastic thin material 124, such as rubber, extends from the leather strip portion 123. The elastic material 124 can be secured by sandwiching it between one layer of the cushioned material 126 and the leather material 122, the elastic material then being glued or heat-sealed therebetween.

The forward end 127 of the toe strap 18 is stitched onto one of the looped ends 128 of a U-shaped hook 130, using the hole 125. The hook 130 itself is sandwiched between a pair of leather tabs 132, 134 and secured therebetween by stitching. The end 127 has its stitching passing not only through the loop 128 but directly into the leather tabs 134.

Connected to the other looped end 136 of the hook 130 is the eye 138 of the wire rod 140 which has a plastic covering 141. The other end of the wire rod has another eye 142 which connects to the metal pin 144 which is secured on to the center portion 146 of the leather strip 56. The pin 144 includes a straight body portion with opposing end hook portions 148, 150. To one hook portion 148 is connected to the eye 142, and the other hook portion 150 is connected to the center portion 146. The latter connection can be by means of stitching.

The layer 132 is sewn over the layer 134 to sandwich the hook 130 therebetween. It is connected by means of suitable stitching. Similarly, a layer 152 is stitched over the center portion 146 by stitching 145 to sandwich the hook 144 therebetween.

One end 155 of thin strip of elastic material 154, such as rubber, is also sandwiched between layers 132, 134. The strip 154 can be glued or heat-sealed to the leather tab 134.

The distal end 156 of the strip 124 is retained by passing it in between the layers 96, 98 of the connecting member 86. It is then passed upward through the slit 110 and then down into the slit 108 so that the distal end 156 is tucked between the layers 96, 98.

Similarly, the distal end 158 of the strip 154 passes through the opposing layers 96, 98 and passes upward through the slit 114 and down through the slit 112 so its distal end 158 is again tucked between the layers 96, 98.

By means of the angular slits 108–114, the ends of the elastic strips 124, 154 can be adjusted so as to adjust the tension in the toe strap.

As shown in FIGS. 4 and 6, the foot supporting device can be utilized on the left foot 159. The toe strap is positioned about the big toe 160. The instep strap 14 is positioned about the forward portion of the instep 161 of the foot 159. The heel strap 12 is positioned about the heel 163. The bands 70, 72 extend across the sole 165 of the foot 159 with the connecting member 86 positioned proximately the ball 167 of the foot and the adjusting member 50 connected forward of the heel portion 163 of the foot. The wire rod 140 extends between the big toe 160 and the second toe 162.

As shown in FIGS. 5 and 7, a corresponding device can be positioned on the right foot 171. The portions of the device are substantially identical to that used for the left foot except that the toe strap 18 now extends to the right side of the instep strap 14 rather than the left side as was utilized in connection with the FIGS. 4 and 6.

As best seen in FIGS. 6 and 7, by adjusting the distal ends 76, 80 of the bands 70, 72, it is possible to adjust the tension in the bands 70, 72 so as to properly provide adequate return movement to the muscles during the relaxation phase.

The bands 70, 72 bend around the rollers in the connecting member 86 and then extend laterally to join the instep strap 14 encircling the instep portion of the foot.

As shown in FIGS. 6 and 7, the elastic rubberized strips 154, 124 cross as they leave the connecting member 86 so as to provide an appropriate fitting on the underside of the big toe.

With the foot supporting device connected, the device provides the necessary pulls on the muscles so as to produce the loosening movements that leads to the relaxation phase of the muscles. The foot supporting device of the present invention is not a rigid support for the arch but is designed to establish a smooth rhythm of tension and relaxation between the steps during which time the foot is stressed with weight-bearing placed upon it. The foot supporting device thereby brings about a relaxation of the foot.

There has been disclosed heretofore the best embodiment of the invention presently contemplated. However, it is to be understood that various changes and modifications may be made thereto without departing from the spirit of the invention.

What is claimed is:

1. A foot supporting device for pulling foot muscles back to a relaxation phase intermediate stress phases placed onto the foot muscles, said device comprising:

an instep strap for disposition around a lower instep portion of a foot, said instep strap including an elongated strip of leather;

first and second elastic bands, one end of said first elastic band being secured to one end of said strip, and one end of said second elastic band being secured to an opposite end of said strip;

a connecting member for disposition proximate the ball of the foot, said connecting member receiving said first and second elastic bands to fittingly maintain said strip around the lower instep portion of the foot, said first and second elastic bands passing through said connecting member;

said connecting member including guide means for directing said first and second elastic bands from a footencircling direction stemming from the opposing ends of said strip to a longitudinal direction along a length of a sole portion of the foot towards a heel portion of the foot;

a heel strap for disposition over the heel portion of the foot;

an adjustment member for disposition on the sole portion of the foot, said adjustment member including adjusting means for adjusting tension in said first and second elastic bands to thereby control any pull along the sole portion of the foot between said instep strap and said heel strap;

said adjustment member including a coupling plate to couple said first and second elastic bands to said heel strap, opposing ends of said heel strap being secured to said coupling plate;

said adjusting means including apertures in said coupling plate for receiving opposite ends of said first and second elastic bands with said opposite ends of said first and second elastic bands projecting out from said coupling plate apertures so that pulling said opposite ends of said first and second elastic bands through said coupling plate apertures provides for adjustment of the tension in said first and second elastic bands; and a toe strap elastically coupled to said connecting member for disposition around the big toe of the foot.

2. A foot supporting device as in claim 1, and further comprising a wire member coupled between said instep strap and said toe strap for disposition between the big toe and the second toe of the foot.

3. A foot supporting device as in claim 2, and comprising eyes coupled to opposing ends of said wire member, one eye being coupled proximate a middle portion of an upper part of said instep strap, the other eye being coupled along said toe strap, whereby said wire member can be manipulated for a desired fit.

4. A foot supporting device as in claim 3, wherein said toe strap comprises a cushioned strip of material, a pair of elastic strips coupled to opposing ends of said cushioned strip, and wherein said other eye is coupled between said cushioned strip and one of said elastic straps.

5. A foot supporting device as in claim 1, wherein said heel strap comprises a pair of arcuate leather strips having a respective one end thereof coupled to said coupling plate, and an elastic band interconnecting respective other ends of said strips.

6. A foot supporting device as in claim 1, wherein said connecting member comprises a pair of opposing connecting plates, a pair of spaced rollers separating said connecting plates, said rollers defining said guide means for directing said elastic bands between said encircling and said longitudinal directions.

7. A foot supporting device as in claim 1, wherein said toe strap comprises a cushioned strip of material, a pair of elastic strips coupled to opposing ends of said cushioned strip, distal ends of said elastic strips being adjustably connected to said connecting member.

8. A foot supporting device as in claim 7, wherein said connecting member contains apertures, the distal ends of said elastic strips being received in said connecting member apertures, whereby pulling the ends of said elastic strips through said connecting member apertures provides adjustment of the toe strap.

9. A foot supporting device as in claim 8, wherein said connecting member apertures are spaced apart, and said elastic strips cross each other prior to being received in said connecting member apertures.

* * * * *